US006395499B1

(12) United States Patent
Abramovitz et al.

(10) Patent No.: US 6,395,499 B1
(45) Date of Patent: May 28, 2002

(54) METHODS OF IDENTIFYING MODULATORS OF A DP PROSTAGLANDIN RECEPTOR

(75) Inventors: Mark Abramovitz, Dollard des Ormeaux; Kathleen Metters, Montreal; Yves Boie, Outremont; Nicole Sawyer, Pincourt; Deborah M. Slipetz, Outremont, all of (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/598,418

(22) Filed: Jun. 20, 2000

Related U.S. Application Data

(62) Division of application No. 09/300,864, filed on Apr. 28, 1999, now Pat. No. 6,214,972, which is a division of application No. 08/812,203, filed on Mar. 6, 1997, now Pat. No. 5,958,723, which is a continuation of application No. 08/378,682, filed on Jan. 26, 1995, now abandoned.

(51) Int. Cl.$^7$ .................. G01N 33/53; G01N 33/567; C07K 1/00; C07K 14/00; C07K 17/00

(52) U.S. Cl. .................. 435/7.2; 435/7.1; 435/7.21; 435/69.1; 530/350

(58) Field of Search .................. 435/7.1, 7.2, 7.21, 435/69.1; 530/350, 300

(56) References Cited

U.S. PATENT DOCUMENTS

| | | |
|---|---|---|
| 5,516,652 A | 5/1996 | Abramovitz |
| 5,605,814 A | 2/1997 | Abramovitz |
| 5,869,281 A | 2/1999 | Abramovitz |
| 5,985,597 A | 11/1999 | Ford-Hutchinson |

FOREIGN PATENT DOCUMENTS

| | | |
|---|---|---|
| WO | WO 94/28125 | 12/1994 |
| WO | WO 95/00551 | 1/1995 |
| WO | WO 95/00552 | 1/1995 |

OTHER PUBLICATIONS

J. Csepli et al. The effect of the prostaglandin F2alpha analogue ICI 81008 on uterine small arteries and on blood pressure.*
(1975). Prostaglandins, 10, pp. 6889–697.*
J. Davis et al. Prostaglandin F2 alpha stimulates phosphatidylinositol 4,5–bisphosphate hydrolysis and mobilizes intracellular Ca2+ in bovine luteal cells. (1987) Proc. Natl. Acad. Sci. U S A. , 84, pp. 3728–3732.*
F. Black et al. Activation of inositol phospholipid breakdown by prostaglandin F2 alpha without any stimulation of proliferation in quiescent NIH–3T3 fibroblasts. (1990)., Biochem. Journal, 266, pp. 661–667.*

Rangachari et al. 'Effects of a Selective DP Receptor Agonists (BW 245C) . . . An Argument for a Different DP Receptor', Jour. of Pharm. and Experimental Thera. Vo. 275, No. 2, (1995).
R. Coleman, et al., Characterisation Of The Prostanoid Receptors Mediating Contraction of Guinea–Pig Isolated Trachea, (1985), Prostaglandins, 29, pp. 363–375.
P. Davies, et. al., Prostaglandins and Inflammation, (1992), Inflammation: Basic Principles And Clinical Correlates, Gallin, Goldstein, Synderman, eds., 2nd Ed., pp. 123–138.
E. Horton, et al., Uterine Luteolytic Hormone: A Physiological Role for Prostaglandin F2a, (1976), Physiol. Rev., 56, pp. 595–651.
D. DeWitt, Prostaglandin endoperoxide synthase: regulation of enzyme expression, (1991), Biochim. Biophys, Acta, 1083, pp. 121–134.
J. Stjernschantz,et al., Phenyl substituted prostaglandin analogs for glaucoma treatment, (1992), Drugs Future, 17, pp. 691–704.
P. Racz, et al., Maintained Intraocular Pressure Reduction With Once–a–Day Application of a New Prostaglandin F2a Analogue (PhXA41), (1993), Arch. Opthalmol., 111, pp. 657–661.
J. Senior, et al., In vitro characterization of prostanoid FP–, DP–, IP– and TP–receptors on the non–pregnant human myometrium, (1992), Brit. J. Pharmacol., 107, pp. 215–221.
J. Senior, et al., In vitro characterization of prostanoid receptors on human myometrium at term pregnancy, (1993), Brit. J. Pharmacol., 108, pp. 501–506.
R. Coleman, Methods in prostanoid receptor classification, (1987), Prostaglandins And Related Substances—A Practical Approach, IRL Press, 1st Ed., pp. 267–303.
R. Coleman, et al., A study of the prostanoid receptors mediating bronchocorstriction in the anaesthetized guinea–pig and dog, (1981), Brit. J. Pharmacol., 74, p. 913.
J. Barnard, et al., Evaluation of prostaglandin F2a and prostacyclin interactions in the isolated perfused rat lung, (1992), J. Appl. Physiol., 72, pp. 2469–2474.
J. Kitanaka, et al., Astrocytes Possess Prostaglandin F2a Receptors Coupled To Phospholipase C, (1991), Biochem. Biophys. Res. Comm., 178, pp. 946–952.
A. Nakao, et al., Characterization of Prostaglandin F2a Receptor of Mouse 3T3 Fibroblasts and Its Functional Expression in Xenopus Laevis Oocytes, (1993), J. Cell Physiol., 155, pp. 257–264.
W. Powell, et al., Prostaglandin F2a Receptor in Ovine corpora lutea, (1974), Eur. J. Biochem., 41, pp. 103–107.

(List continued on next page.)

*Primary Examiner*—Gary L. Kunz
*Assistant Examiner*—Robert S. Landsman
(74) *Attorney, Agent, or Firm*—J. Mark Hand; Jack L. Tribble

(57) ABSTRACT

A human prostaglandin receptor has been identified and DNA encoding the receptor has been isolated, purified, sequenced and expressed in host cells. This DNA encoding the human prostaglandin receptor and host cells expressing the receptor are used to identify modulators of the prostaglandin receptor.

17 Claims, 4 Drawing Sheets

OTHER PUBLICATIONS

W. Powell, et al., Occurrence and Properties of a Prostaglandin F2a Receptor in Bovine Corpora Lutea, (1975), Eur. J. Biochem., 56, pp. 73–77.

W. Powell, et al., Localization of a Prostaglandin F2a Receptor in Bovine Corpus luteum Plasma Membranes, (1976), Eur. J. Biochem., 61, pp. 605–611.

M. Molnar, et al., PGF2a and PGE2 binding to rat myometrium during gestation, parturition, and postpartum, (1990), Am. J. Physiol., 258, pp. E740–E747.

Th. Bauknecht, et al., Distribution of prostaglandin E2 and prostaglandin F2a, receptors in human myometrium, (1981), Acta Endocrinol., 98, pp. 446–450.

F. Neuschafer–Rube, et al., Characterization of prostaglandin–F2a–binding sites on rat hepatocyte plasma membranes, (1993), Eur. J. Biochem., 211, pp. 163–169.

M. Hirata, et al., Cloning and expression of cDNA for a human thromboxane A2 receptor, (1991), Nature, 349, pp. 617–620.

A. Honda, et al., Cloning and Expression of a cDNA for Mouse Prostaglandin E Receptor EP2 Subtype, (1993), J. Biol. Chem., 268, pp. 7759–7762.

Y. Sugimoto, et al., Two Isoforms of the EP3 Receptor with Different Carboxyl–terminal Domains, (1993), J. Biol. Chem., 268, pp. 2712–2718.

Y. Sugimoto, et al., Cloning and Expression of a cDNA for Mouse Prostaglandin E Receptor EP3 Subtype, (1992), J. Biol. Chem., 267, pp. 6463–6466.

K. Bunce, et al., Differential Effects Of Prostaglandins On Unidirectional Absorption And Secretion In Rat Ileum, (1987), Gastroenterology, 92, p. 1332.

Y. Dong, et al., Prostaglandin E receptor subtypes in smooth muscle: agonist activities of stable prostacyclin analogues, (1986), Br. J. Pharmacol., 87, pp. 97–107.

B. Hedqvist, et al., Prostaglandin–Induced Neurotransmission Failure In The Field–Stimulated, Isolated Vas Deferens, (1972), Neuropharmacology, 11, pp. 177–187.

M. McKenniff, et. al., Characterisation of receptors mediating the contractile effects of prostanoids In guinea–pig and human airways, (1988), Eur. J. Pharmacol., 153, pp. 149–159.

R. Eglen, et al., The action of prostanoid receptor agonists and antagonists on smooth muscle and platelets, (1988), Br. J. Pharmacol., 94, pp. 591–601.

J. Louttit, et al., Prostanoid EP–Receptors in Pig Saphenous Vein, (7/26–31/92) , 8th International Conf. on Prostaglandins, Abstract 258.

R. Lawrence, et al., Investigation of the prostaglandin E (EP–) receptor subytpe mediating relaxation of the rabbit jugular vein, (1992), Br. J. Pharmacol., 105, pp. 817–824.

R. Coleman, et al., Prostanoids and their Receptors, (1989), Comprehensive Medicinal Chemistry, 3, pp. 643–714.

W. Campbell, et al., Lipid–Derived Autacoids: Eicosanoids And Platelet–Activating Factor, (1990), The Pharmacological Basis of Therapeutics, 8th Edition, pp. 600–617.

Adie et al., 'Concurrent down–regulation of IP prostanoid receptors . . . glioma cells to prostanoid agonists' Biochem. J., vol. 285, pp 529–536 (1992).

Negishi et al., 'Prostanoid Receptors and their Biological Actions',, Prog. Lipid Res., vol. 32, pp 417–434 (1993).

Coleman et al., 'VIII. International Union of Pharmacology . . . and their Subtypes', Pharm. Reviews, vol. 46, pp. 205–229 (1994).

Ito et al., 'Prostaglandin D2: A Biochemical Perspective', Prostaglandins Leutrokienes and Essential Fatty Acids, vol. 37, pp 219–234 (1989).

Woodward et al. 'Further studies on ocular responses to DP receptor stimulation', European J. Pharm. vol. 230, pp 327–333 (1993).

Nakajima et al. Graefe's Arch. Clin. Exp. Tphthalmol. 229: 411–413 (1991).

Hirata et al. 'Molecular characterization of a mouse prostaglandin D receptor and functional expression of the cloned gene', PNAS, vol. 91, pp 11192–11196 (1994).

Virgolini et al. 'Characterization of Prostaglandin (PG)–binding Sites Expressed on Human Basophils', J. Biol. Chem., vol. 267, pp 12700–12708 (1992).

Katsuyama 'Cloning and expression of cDNA for human prostacyclin receptor', FEBS Letters, vol. 344, pp 74–78 (1994).

Boie et al, 'Molecular Cloning and Characterization of the Human Prostanoid DP Receptor', J. Biol. Chem. vol. 270, No. 32, pp 18910–6 (1995).

Boie, 'Molecular Cloning and Characterization of the Human DP Prostanoid Receptor', FASEB Jour. vol. 9, No. 6 (1995).

Narumiya et al. 'Prostanoid Receptors: Molecular Structures, Functions and Distributions', Nineth International Conf p 1 (1994).

Narumiya et al. 'Structures, Properties, and Distributions of Prostanoid Receptors', Ninth International Conf. pp 17–22 vol. 23, (1995).

An S, et al. Cloning and expression of the EP2 type of human receptors for prostaglandin E2. Biochem. Biophys. Res. Comm. 197:263–270, 1993.*

Hirata M, et al. Molecular characterization of a mouse prostaglandin D receptor and functional expression of the cloned gene. Proc. Natl. Acad. Sci. USA. 91:11192–11196, 1994.*

Honda A, et al. Cloning and expression of a cDNA for mouse prostaglandin E receptpor EP2 subtype. J. Biol. Chem. 268:7759–7762, 1993.*

* cited by examiner

```
GAATTCTGGC TATTTTCCTC CTGCCGTTCC GACTCGGCAC CAGAGTCTGT
CTCTACTGAG AACGCAGCGC GTCAGGGCCG AGCTCTTCAC TGGCCTGCTC
CGCGCTCTTC AATGCCAGCG CCAGGCGCTC ACCCTGCAGA GCGTCCCGCC
TCTCAAAGAG GGGTGTGACC CGCGAGTTTA GATAGGAGGT TCCTGCCGTG
GGGAACACCC CGCCGCCCTC GGAGCTTTTT CTGTGGCGCA GCTTCTCCGC
CCGAGCCGCG CGCGGAGCTG CCGGGGGCTC CTTAGCACCC GGGCGCCGGG
GCCCTCGCCC TTCCGCAGCC TTCACTCCAG CCCTCTGCTC CGCACGCCA
TGAAGTCGCC GTTCTACCGC TGCCAGAACA CCACCTCTGT GGAAAAAGGC
AACTCGGCGG TGATGGGCGG GGTGCTCTTC AGCACCGGCC TCCTGGGCAA
CCTGCTGGCC CTGGGGCTGC TGGCGCGCTC GGGGCTGGGG TGGTGCTCGC
GGCGTCCACT GCGCCCGCTG CCCTCGGTCT TCTACATGCT GGTGTGTGGC
CTGACGGTCA CCGACTTGCT GGGCAAGTGC CTCCTAAGCC CGGTGGTGCT
GGCTGCCTAC GCTCAGAACC GGAGTCTGCG GGTGCTTGCG CCCGCATTGG
ACAACTCGTT GTGCCAAGCC TTCGCCTTCT TCATGTCCTT CTTTGGGCTC
TCCTCGACAC TGCAACTCCT GGCCATGGCA CTGGAGTGCT GGCTCTCCCT
AGGGCACCCT TTCTTCTACC GACGGCACAT CACCCTGCGC CTGGGCGCAC
TGGTGGCCCC GGTGGTGAGC GCCTTCTCCC TGGCTTTCTG CGCGCTACCT
TTCATGGGCT TCGGGAAGTT CGTGCAGTAC TGCCCCGGCA CCTGGTGCTT
TATCCAGATG GTCCACGAGG AGGGCTCGCT GTCGGTGCTG GGGTACTCTG
TGCTCTACTC CAGCCTCATG GCGCTGCTGG TCCTCGCCAC CGTGCTGTGC
AACCTCGGCG CCATGCGCAA CCTCTATGCG ATGCACCGGC GGCTGCAGCG
GCACCCGCGC TCCTGCACCA GGGACTGTGC CGAGCCGCGC GCGGACGGGA
GGGAAGCGTC CCCTCAGCCC CTGGAGGAGC TGGATCACCT CCTGCTGCTG
GCGCTGATGA CCGTGCTCTT CACTATGTGT TCTCTGCCCG TAATTTATCG
CGCTTACTAT GGAGCATTTA AGGATGTCAA GGAGAAAAAC AGGACCTCTG
AAGAAGCAGA AGACCTCCGA GCCTTGCGAT TTCTATCTGT GATTTCAATT
GTGGACCCTT GGATTTTTAT CATTTTCAGA TCTCCAGTAT TTCGGATATT
TTTTCACAAG ATTTTCATTA GACCTCTTAG GTACAGGAGC CGGTGCAGCA
ATTCCACTAA CATGGAATCC AGTCTGTGAC AGTGTTTTTC ACTCTGTGGT
AAGCTGAGGA ATATGTCACA TTTTCAGTCA AAGAACCA (SEQ ID NO: 4)
```

FIG.1

MKSPFYRCQNTTSVEKGNSAVMGGVLFSTGLLGNLLALGLLARSGL
GWCSRRPLRPLPSVFYMLVCGLTVTDLLGKCLLSPVVLAAYAQNRS
LRVLAPALDNSLCQAFAFFMSFFGLSSTLQLLAMALECWLSLGHPFF
YRRHITLRLGALVAPVVSAFSLAFCALPFMGFGKFVQYCPGTWCFIQ
MVHEEGSLSVLGYSVLYSSLMALLVLATVLCNLGAMRNLYAMHRR
LQRHPRSCTRDCAEPRADGREASPQPLEELDHLLLLALMTVLFTMCS
LPVIYRAYYGAFKDVKEKNRTSEEAEDLRALRFLSVISIVDPWIFIIFR
SPVFRIFFHKIFIRPLRYRSRCSNSTNMESSL (SEQ ID NO: 3)

FIG.2

METHODS OF IDENTIFYING MODULATORS OF A DP PROSTAGLANDIN RECEPTOR

This application is a division of application Ser. No. 09/300,864, filed Apr. 28, 1999, which issued as U.S. Pat. No. 6,214,972, which is a division of application Ser. No. 08/812,203, filed Mar. 6, 1997, which issued as U.S. Pat. No. 5,958,723, which is a continuation of application Ser. No. 08/378,682, filed Jan. 26, 1995, abandoned.

BACKGROUND OF THE INVENTION

Prostaglandin $D_2$ ($PGD_2$) is synthesized in a number of tissues including brain, spleen, lung, mast cells, bone marrow, stomach, skin and eye (Negishi M., et al., Prog. Lipid Res. 32:417–434, 1993, and references within). Central nervous system actions of $PGD_2$ are thought to involve effects on sleep induction, body temperature, olfactory function, hormone release, inflammation and analgesia (Negishi M., et al., supra, and references within). $PGD_2$ can cause inhibition of platelet aggregation (Coleman R. A., et al., Pharmacological Reviews 46:205–229, 1994, and references within). $PGD_2$ is also the predominant prostanoid released from mast cells upon immunologic challenge and as such is thought to be a mediator of various allergic disorders including but not limited to allergic rhinitis and airway hyperreactivity (Ito S. et al., Prostaglandins Leukotrienes and Essential Fatty Acids. 37:219–234, 1989, and references within). It may also stimulate secretion in the intestine. Topically applied $PGD_2$ has also been shown to reduce intraoccular pressure (Woodward D. F., et al. European J. Pharmacology. 230:327–333, 1993, and Nakajima M., et al., Graefe's Arch. Clin. Exp. Ophthalmol. 229:411–413, 1991).

The physiological actions of $PGD_2$ are mediated through interaction with the prostanoid DP receptor. The DP receptors are thought to be distributed mainly in blood platelets, smooth muscle of various tissues and nervous tissue, including the central nervous system (Coleman R. A., et al., supra, and references within). However, the DP receptor is the least ubiquitous and least abundant of the prostanoid receptors and as such is the one least well characterized. To further complicate matters many of the actions of $PGD_2$ and distribution of their receptor are also species dependent. Specific binding sites for the DP receptor have been tentatively studied using human platelet membranes, rat brain synaptic membranes and membranes prepared from a cell line derived from bovine embryonic trachea (Coleman R. A., et al., supra, and references within).

The above methods for studying DP receptor activities have several disadvantages in that most if not all preparations contain several different but related prostanoid receptor populations, each with different ligand binding properties, making measurements of absolute potency and selectivity very unpredictable. In addition, the low abundance of the DP receptor in various tissues or cells makes it very difficult to satisfactorily test for compounds as modulators, effectors, agonists or antagonists, of the human DP receptor.

SUMMARY OF THE INVENTION

A novel prostaglandin receptor protein termed DP has been identified from human cells. A DNA molecule encoding the full length DP protein has been isolated and purified, and the nucleotide sequence has been determined. The DP encoding DNA has been cloned into expression vectors and these expression vectors, when introduced into recombinant host cells, cause the recombinant host cells to express a functional DP receptor protein. The novel DP protein, the DP-encoding DNA, the expression vectors and recombinant host cells expressing recombinant DP are useful in the identification of modulators of DP receptor activity.

A method of identifying DP receptor modulators is also disclosed which utilizes the recombinant DP expressing host cells.

Modulators of DP activity are useful for the treatment of prostaglandin-related diseases and for modulating the effects of prostaglandins on the DP receptor.

BRIEF DESCRIPTION OF THE DRAWINGS

FIG. 1—The DNA sequence of human DP cDNA construct is shown.

FIG. 2—The complete deduced amino acid sequence of the DP receptor protein is shown.

DETAILED DESCRIPTION OF THE INVENTION

Figure 3:
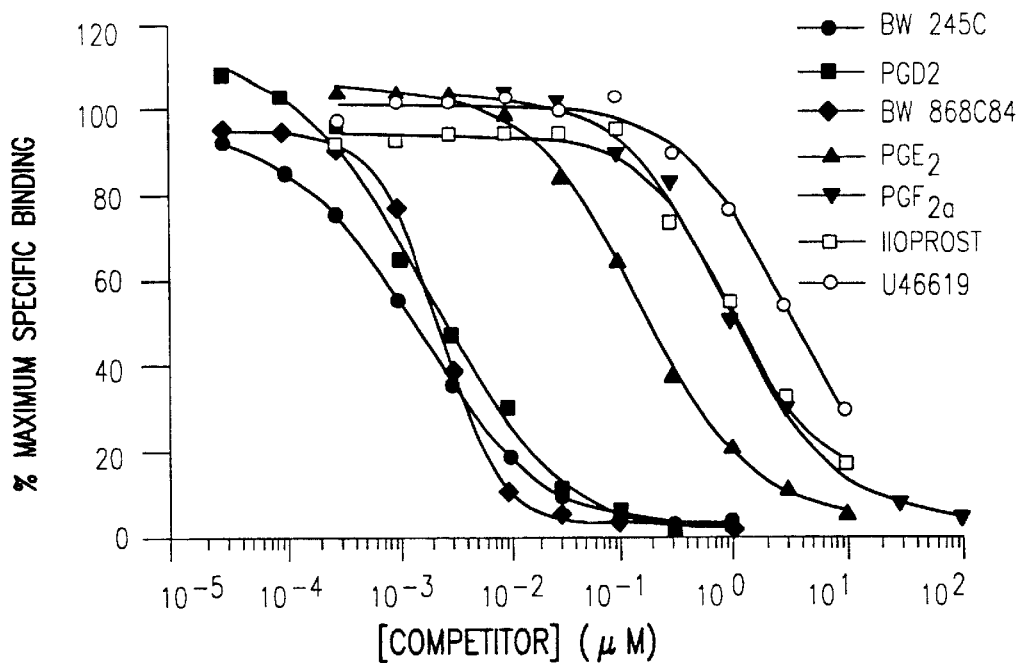
FIG. 3—Competition for [$^3$H]$PGD_2$ specific binding to pcDNA3-hDP transfected COS-M6 membranes. [$^3$H]$PGD_2$ binding assays were performed as described in Example 6. The percentage maximum [$^3$H]$PGD_2$ specific binding at each competing ligand concentration was determined for $PGD_2$ (■), the DP receptor agonist BW245C (●), the DP antagonist BW868C (♦), $PGE_2$ (▲), $PGF_{2\alpha}$ (▼), iloprost (□) and the TP-receptor agonist U46619 (○), over a concentration range up to 100 $\mu$M.
Figure 4:
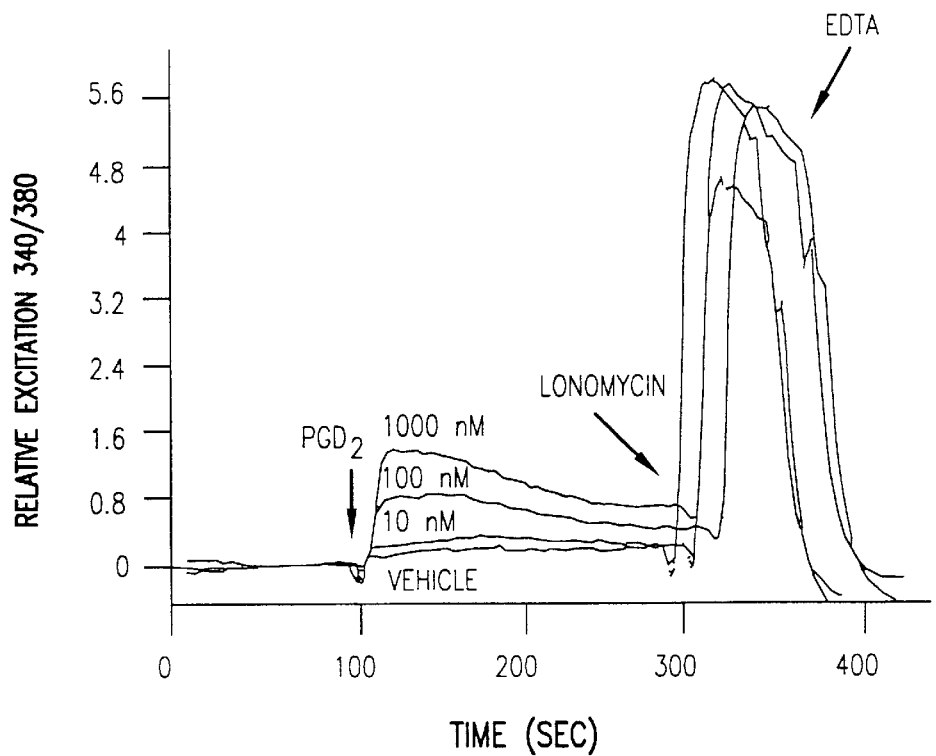
FIG. 4—Increases in intracellular calcium [$Ca^{2+}$]i in HEK293 (EBNA) cells stably expressing the DP receptor is shown. DP-HEK293 (EBNA) cells were harvested and prepared as described in Example 8. DP-HEK293 (EBNA) cells were then challenged with vehicle ($Me_2SO_4$ at 0.2% v/v final), or 10 nM, 100 nM or 1,000 nM $PGD_2$. At the end of each experiment cells were challenged with 1 $\mu$M ionomycin to release [$Ca^{2+}$]i followed by quenching of the [$Ca^{2+}$]i release with 1 mM EDTA.
Figure 5:
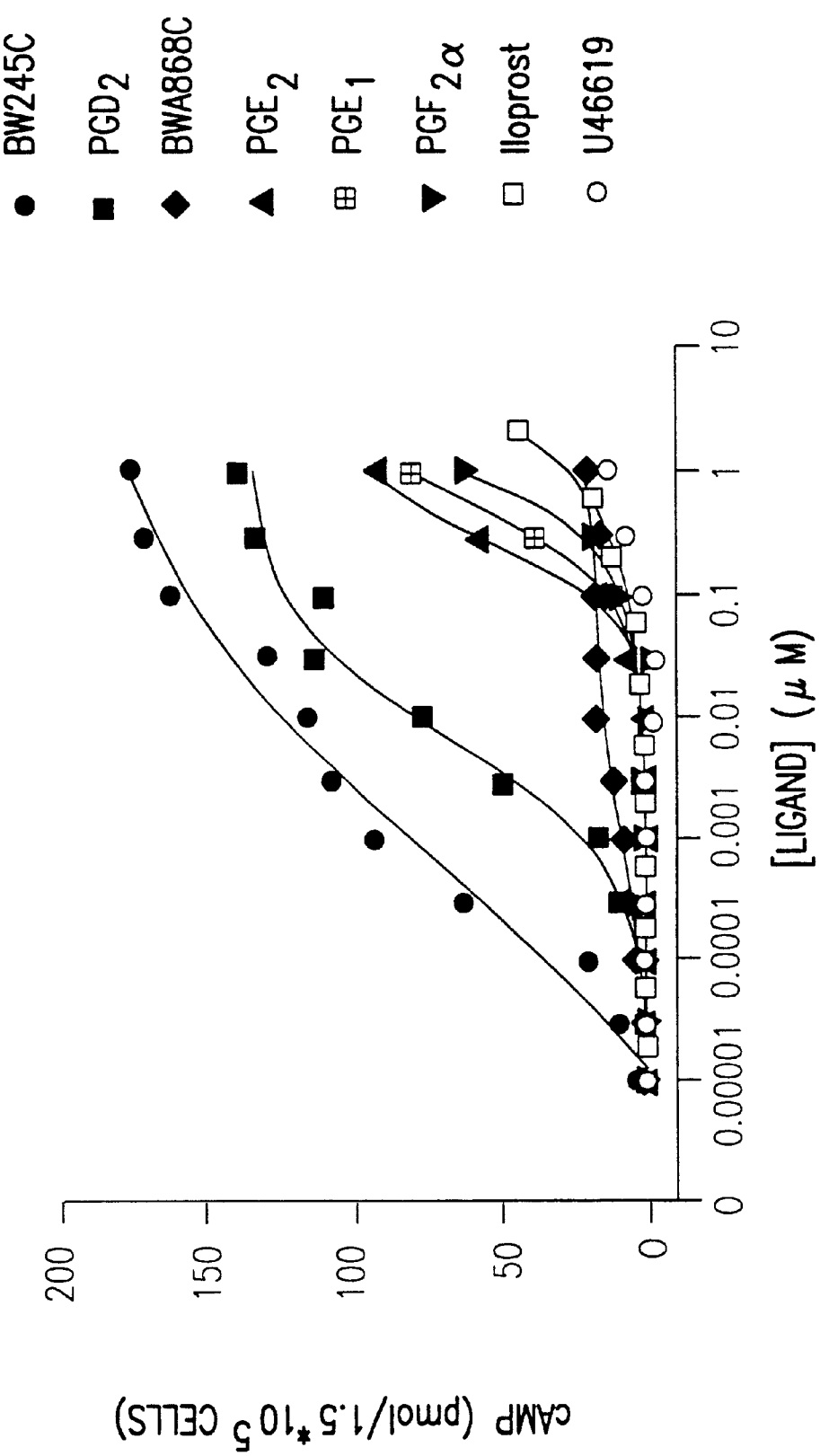
FIG. 5—Increases in intracellular cAMP production in HEK293 (EBNA) cells stably expressing the DP receptor is shown. cAMP assays were performed as described in Example 7. The pmoles of cAMP produced per $1.5 \times 10^5$ cells at each ligand concentration was determined for $PGD_2$ (n), the DP receptor agonist BW245C (●), the DP antagonist BW868C (♦), $PGE_2$ (▲), $PGE_1$ (⊞), $PGF_{2\alpha}$ (▼), iloprost (□) and the TP-receptor agonist U46619 (○), over a concentration range up to 1 $\mu$M.

The present invention relates to DNA encoding a novel prostaglandin receptor, termed DP. The present invention is also related to recombinant host cells which express the cloned DP-encoding DNA contained in a recombinant expression plasmid. The present invention is also related to methods for the screening of substances which modulate DP receptor activity. The DNA of the present invention is isolated from genomic DNA and DNA from DP producing cells. DP, as used herein, refers to a G protein-coupled receptor which can specifically bind prostaglandin molecules.

Mammalian cells capable of producing DP include, but are not limited to, cells derived from the small intestine, smooth muscle such as vascular, respiratory and reproductive, eye and platelets. Transformed mammalian cell lines which produce DP include, but are not limited to, cells derived from bovine embyonic trachea. The preferred cells for the present invention include normal human retina, platelets and the most preferred cells are human small intestine cells.

Other cells and cell lines may also be suitable for use to isolate DP cDNA. Selection of suitable cells may be done by Northern blot analysis, radioligand binding analysis, fuctional analysis or by screening for DP on cell surfaces. Methods for detecting DP activity are well known in the art and measure the binding of radiolabelled ligand specific for the receptor. Cells which possess DP activity in this assay may be suitable for the isolation of DP cDNA.

Any of a variety of procedures may be used to clone DP cDNA. These methods include, but are not limited to, direct functional expression of the DP cDNA following the construction of an DP-containing cDNA library in an appropriate expression vector system. Another method is to screen a DP-containing cDNA library constructed in a bacteriophage or plasmid shuttle vector with a labelled oligonucleotide probe designed from the amino acid sequence of the DP protein. The preferred method consists of screening a genomic or DP-containing cDNA library constructed in a bacteriophage or plasmid shuttle vector with a partial cDNA encoding the DP protein. This partial cDNA is obtained by the specific PCR amplification of DP DNA fragments through the design of degenerate oligonucleotide primers from the amino acid sequence known for other G protein-coupled receptors which are related to the prostaglandin DP receptors.

It is readily apparent to those skilled in the art that other types of libraries, as well as libraries constructed from other cells or cell types, may be useful for isolating DP-encoding DNA. Other types of libraries include, but are not limited to, cDNA libraries derived from other cells or cell lines and genomic DNA libraries.

It is readily apparent to those skilled in the art that suitable cDNA libraries may be prepared from cells or cell lines which have DP activity. The selection of cells or cell lines for use in preparing a cDNA library to isolate DP cDNA may be done by first measuring cell associated DP activity using the known radiolabelled ligand binding assay cited above and used herein.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual (Cold Spring Harbor Laboratory, Cold Spring Harbor, N.Y., 1989).

It is also readily apparent to those skilled in the art that DNA encoding DP may also be isolated from a suitable genomic DNA library. Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manual (Cold Spring Harbor Laboratory, Cold Spring Harbor, N.Y., 1989).

In order to clone the DP gene by one of the preferred methods, the amino acid sequence or DNA sequence of DP or a homologous protein is necessary. To accomplish this, DP protein or a homologous protein may be purified and partial amino acid sequence determined by automated sequenators. It is not necessary to determine the entire amino acid sequence, but the linear sequence of two regions of 6 to 8 amino acids can be determined for the PCR amplification of a partial DP DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the DP sequence but others in the set will be capable of hybridizing to DP DNA even in the presence of DNA oligonucleotides with mismatches. The mismatched DNA oligonucleotides may still sufficiently hybridize to the DP DNA to permit identification and isolation of DP encoding DNA.

Using one of the preferred methods, cDNA clones encoding DP are isolated in a two-stage approach employing polymerase chain reaction (PCR) based technology and cDNA library screening. In the first stage, $NH_2$-terminal and internal amino acid sequence information from the purified DP or a homologous protein is used to design degenerate oligonucleotide primers for the amplification of DP-specific DNA fragments. In the second stage, these fragments are cloned to serve as probes for the isolation of full length cDNA from cDNA libraries.

The sequence for the cDNA encoding DP is shown in FIG. 1. The deduced amino acid sequence of DP from the cDNA is shown in FIG. 2. Inspection of the determined cDNA sequence reveals the presence of a single, large open reading frame that encodes for an approximately 359 amino acid protein.

The cloned DP cDNA obtained through the methods described above may be recombinantly expressed by molecular cloning into an expression vector containing a suitable promoter and other appropriate transcription regulatory elements, and transferred into prokaryotic or eukaryotic host cells to produce recombinant DP. Techniques for such manipulations can be found described in Maniatis, T, et al., supra, and are well known in the art.

Expression vectors are defmed herein as DNA sequences that are required for the transcription of cloned DNA and the translation of their mRNAs in an appropriate host. Such vectors can be used to express eukaryotic DNA in a variety of hosts such as bacteria, bluegreen algae, fungal cells, plant cells, insect cells and animal cells.

Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant DP in mammalian cells. Commercially available mammalian expression vectors which may be suitable for recombinant DP expression, include but are not limited to, pMC1neo (Stratagene), pXT1 (Stratagene), pSG5 (Stratagene), pcDNAI, pcDNAIamp, pcDNA3 (Invitrogen), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), IZD35 (ATCC 37565), and vaccinia virus transfer vector pTM1.

DNA encoding DP may also be cloned into an expression vector for expression in a host cell. Host cells may be prokaryotic or eukaryotic, including but not limited to bacteria, yeast, mammalian cells including but not limited to cell lines of human, bovine, porcine, monkey and rodent origin, and insect cells including but not limited to Sf9 and drosophila derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, infection, protoplast fusion, and electroporation. The expression vector-containing cells are individually analyzed to determine whether they produce DP protein. Identification of DP expressing cells may be done by several means, including but not limited to immunological reactivity with anti-DP antibodies, and the presence of host cell-associated DP activity.

Expression of DP DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the DP cDNA sequence(s) that yields optimal levels of receptor activity and/or DP protein, DP cDNA molecules including but not limited to the following can be constructed: the full-length open reading frame of the DP cDNA and various constructs containing portions of the cDNA encoding only specific domains of the receptor protein or rearranged domains of the protein. All constructs can be designed to contain none, all or portions of the 5' and/or 3' untranslated region of DP cDNA. DP activity and levels of protein expression can be determined following the introduction, both singly and in combination, of these constructs into appropriate host cells. Following determination of the DP cDNA cassette yielding optimal expression in transient assays, this DP cDNA construct is transferred to a variety of expression vectors (including recombinant viruses), including but not limited to those for mammalian cells, plant cells, insect cells, oocytes, E. coli, fungal and yeast cells.

Mammalian cell transfectants are assayed for both the levels of DP receptor activity and levels of DP protein by the following methods. Assessing DP receptor activity involves the direct introduction of a radiolabelled ligand to the cells and determining the amount of specific binding of the radioligand to the DP-expressing cells. Binding assays for receptor activity are known in the art (Frey et al., 1993, Eur. J. Pharmacol., 244, pp 239–250).

Levels of DP protein in host cells is quantitated by a variety of techniques including, but not limited to, immunoaffinity and/or ligand affinity techniques. DP-specific affinity beads or DP-specific antibodies are used to isolate $^{35}$S-methionine labelled or unlabelled DP protein. Labelled DP protein is analyzed by SDS-PAGE. Unlabelled DP protein is detected by Western blotting, ELISA or RIA assays employing DP specific antibodies.

Following expression of DP in a host cell, DP protein may be recovered to provide DP in active form, capable of binding DP-specific ligands. Several DP purification procedures are available and suitable for use. Recombinant DP may be purified from cell membranes by various combinations of, or individual application of standard separation techniques including but not limited to detergent solubilization, salt fractionation, ion exchange chromatography, size exclusion chromatography, hydroxylapatite adsorption chromatography and hydrophobic interaction chromatography.

In addition, recombinant DP can be separated from other cellular proteins by use of an immuno-affinity column made with monoclonal or polyclonal antibodies specific for full length nascent DP, or polypeptide fragments of DP.

Monospecific antibodies to DP are purified from mammalian antisera containing antibodies reactive against DP or are prepared as monoclonal antibodies reactive with DP using the technique of Kohler and Milstein, Nature 256: 495–497 (1975). Monospecific antibody as used herein is defined as a single antibody species or multiple antibody species with homogenous binding characteristics for DP. Homogenous binding as used herein refers to the ability of the antibody species to bind to a specific antigen or epitope, such as those associated with the DP, as described above. DP specific antibodies are raised by immunizing animals such as mice, rats, guinea pigs, rabbits, goats, horses and the like, with an appropriate concentration of DP or a peptide derived from the sequence of the DP protein either with or without an immune adjuvant.

Preimmune serum is collected prior to the first immunization. Each animal receives between about 0.1 mg and about 1000 mg of DP or DP-related peptide associated with an acceptable immune adjuvant. Such acceptable adjuvants include, but are not limited to, Freund's complete, Freund's incomplete, alum-precipitate, water in oil emulsion containing Corynebacterium parvum and tRNA. The initial immunization consisted of the DP or DP-related peptide in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of DP or DP-related peptide in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with DP or a peptide derived from the sequence of the DP protein are prepared by immunizing inbred mice, preferably Balb/c, with DP or DP-related peptide. The mice are immunized by the DP or SC route with about 1 mg to about 100 mg, preferably about 10 mg, of DP or DP-related peptide in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 mg of DP in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using DP or DP-related peptide as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristine primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-DP mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of DP in body fluids or tissue and cell extracts.

It is readily apparent to those skilled in the art that the above described methods for producing monospecific antibodies may be utilized to produce antibodies specific for DP polypeptide fragments, or full-length DP polypeptide.

DP antibody affinity columns are made by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing DP or DP fragments are slowly passed through the column. The column is then washed with phosphate buffered saline together with appropriate membrane solubilizing agent such as detergents until the optical density ($A_{280}$) falls to background, then the protein is eluted with 0.23 M glycine-HCl (pH 2.6) together with appropriate membrane solubilizing agents such as detergents. The purified DP protein is then dialyzed against phosphate buffered saline together with appropriate membrane solubilizing agent, such as detergents.

One method suitable for the isolation of DNA encoding the prostaglandin receptor of the present invention involves the utilization of amino acid and/or DNA sequence information obtained from other G-protein-linked receptors. Since other prostaglandin receptors are known to be G-protein linked, certain regions or domains such as the transmembrane and/or cytoplasmic domains, are expected to have some degree of homology sufficient to produce a probe for the isolation of novel receptors.

Prostaglandins and leukotrienes are known to transduce their signals via G-protein-linked receptors. Distinct receptors for $PGH_2$ thromboxane $A_2$, $PGI_2$, $PGE_2$, $PGD_2$, $PGF_{2\alpha}$, $LTB_4$, and $LTD_4$ present in various tissues have been described. Some of the receptors have been solubilized and partially purified (Dutta-Roy, A. K. et al., (1987) JBC, 262, pp. 12685; Tsai, A. L. et al., (1989), JBC, 264, pp 61; 168—Watanabe, T. et. al., (1990), JBC, 265, pp. 21237) and the human platelet $TX_{A2}$ receptor has been purified to apparent homogeneity (Ushikubi, F. et. al., (1989), JBC, 264, pp. 16496). The purified thromboxane receptor exhibited a very broad band on a SDS-polyacrylamide gel centered at appr. 57 kDa. Enough protein was obtained for partial sequence information.

One approach to the isolation of other eicosanoid receptor genes by homology screening can be taken, with the assumption that these receptors are related in primary structure (Sugimoto, Y. et al., (1992), JBC, 267, pp. 6463). Since these receptors are of the G-protein-coupled receptor superfamily there are areas of homology which are likely to be found in the transmembrane region and in the cytoplasmic domains. Therefore, various known G-protein linked receptors related to the prostaglandin receptors may be utilized to provide DNA probes to regions of the receptor protein-encoding DNA sought, which is likely to have homology, such as the transmembrane region.

Another approach relies on the homology that exists for a given receptor between mammalian species. The degree of relatedness at the level of the amino acid sequence usually, but not always, ranges from 60 to 95%. A partial cDNA probe for one receptor from mouse can be used to screen for the human homolog.

Using the above approach a partial cDNA probe for the mouse DP receptor (the amino acid sequence for which was presented by Dr. Shuh Narumiya from Kyoto University, Japan, at the 9th International Conference on Prostaglandins and Related Compounds, Florence, Italy, Jun. 6–10, 1994) was made by ampifying a 5' DNA fragment from mouse genomic DNA by using the polymerase chain reaction (PCR). This cDNA was then used as a probe to obtain a clone for the human DP receptor gene which did not contain the sequence coding for the C-terminal portion of the protein. In order to obtain the cDNA which would encode the full length hDP receptor the 5' end of the genomic clone was combined with a 3' fragment generated by 3' RACE (rapid amplification of cDNA ends) PCR. This constructed cDNA now contained one large open reading frame which codes for the human DP receptor. Like many other G-protein coupled receptors, the DP receptor shares several common features. Firstly, there are seven predicted transmembrane domains by hydrophobicity analysis. Secondly, conserved cysteine residues are found in extracellular loops 1 and 2. Thirdly, the DP receptor possesses a conserved arginine found in all known eicosanoid receptors within transmembrane seven. This region is the most highly conserved among the eicosanoid receptors.

The novel prostaglandin receptor of the present invention is suitable for use in an assay procedure for the identification of compounds which modulate the receptor activity. Modulating receptor activity, as described herein includes the inhibition or activation of the receptor and also includes directly or indirectly affecting the normal regulation of the receptor activity. Compounds which modulate the receptor activity include agonists, antagonists and compounds which directly or indirectly affect regulation of the receptor activity.

The prostaglandin receptor of the present invention may be obtained from both native and recombinant sources for use in an assay procedure to identify receptor modulators. In general, an assay procedure to identify prostaglandin receptor modulators will contain the prostaglandin receptor of the present invention, and a test compound or sample which contains a putative prostaglandin receptor modulator. The test compounds or samples may be tested directly on, for example, purified receptor protein whether native or recombinant, subcellular fractions of receptor-producing cells whether native or recombinant, and/or whole cells expressing the receptor whether native or recombinant. The test compound or sample may be added to the receptor in the presence or absence of a known labelled or unlabelled receptor ligand. The modulating activity of the test compound or sample may be determined by, for example, analyzing the ability of the test compound or sample to bind to the receptor, activate the receptor, inhibit receptor activity, inhibit or enhance the binding of other compounds to the receptor, modify receptor regulation, or modify an intracellular activity.

The identification of modulators of DP receptor activity are useful in treating disease states involving the DP receptor activity. Other compounds may be useful for stimulating or inhibiting activity of the receptor. Selective agonists or antagonists of the DP receptor may be of use in the treatment of diseases and disease states including but not limited to, glaucoma, allergic rhinitis and any other allergic disorders in which mast cells are involved, sleep disorders, and may have utility in the inhibition of platelet aggregation and hence in the treatment of vascular diseases, prevention of post-injury blood clotting and rejection in organ tranplantation and by-pass surgery, congestive heart failure, pulmonary hypertension, gangrene, Raynaud's disease, bone resorption, shock, and gastric acid secretion. Modulators may also be useful as cytoprotective and antiinflammatory agents. The isolation and purification of an DP-encoding DNA molecule would be useful for establishing the tissue distribution of DP receptors, studying changes in DP receptor expression in disease states, as well as establishing a process for identifying compounds which modulate DP receptor activity.

The present invention is also directed to methods for screening for compounds which modulate the expression of DNA or RNA encoding DP receptor as well as the function of DP receptor protein in vivo. Compounds which modulate these activities may be DNA, RNA, peptides, proteins, or non-proteinaceous organic molecules. Compounds may modulate by increasing or attenuating the expression of DNA or RNA encoding DP receptor, or the function of DP receptor protein. Compounds that modulate the expression of DNA or RNA encoding DP receptor or the function of DP receptor protein may be detected by a variety of assays. The assay may be a simple "yes/no" assay to determine whether there is a change in expression or function. The assay may be made quantitative by comparing the expression or function of a test sample with the levels of expression or function in a standard sample. Modulators identified in this process are useful as therapeutic agents, insecticides and helminthicides.

Kits containing DP receptor DNA, RNA, antibodies to DP receptor, or DP receptor protein may be prepared. Such kits are used, for example, to detect DNA which hybridizes to DP receptor DNA or to detect the presence of, and/or quantify, DP receptor protein or peptide fragments in a sample. Such characterization is useful for a variety of purposes including but not limited to forensic analyses, monitoring the course of therapy, and epidemiological studies.

The DNA molecules, RNA molecules, recombinant protein and antibodies of the present invention may be used to screen and measure levels of DP receptor DNA, DP receptor RNA or DP receptor protein. The recombinant proteins, DNA molecules, RNA molecules and antibodies lend themselves to the formulation of kits suitable for the detection, quantification, and typing of DP receptor. Such a kit would comprise, for example, a compartmentalized carrier suitable to hold in close confinement at least one container. The carrier would further comprise reagents such as recombinant DP receptor protein or anti-DP receptor antibodies suitable for detecting DP receptor. The carrier may also contain a means for detection such as labeled antigen or enzyme substrates or the like.

Nucleotide sequences that are complementary to the DP receptor encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other DP receptor antisense oligonucleotide mimetics. DP receptor antisense molecules may be introduced into cells by methods known in the art, including microinjection, liposome encapsulation or by expression from vectors harboring the antisense sequence. DP receptor antisense therapy may be particularly useful for the treatment of diseases where it is beneficial to reduce DP receptor activity.

DP receptor gene therapy may be used to introduce DP receptor into the cells of target organisms. The DP receptor gene can be ligated into, for example, viral vectors which mediate transfer of the DP receptor DNA by infection of recipient host cells. Suitable viral vectors include retrovirus, adenovirus, adeno-associated virus, herpes virus, vaccinia virus, polio virus and the like. Alternatively, DP receptor DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo DP receptor gene therapy. DP receptor gene therapy may be particularly useful for the treatment of diseases where it is beneficial to elevate DP receptor activity.

Pharmaceutically useful compositions comprising DP receptor DNA, DP receptor RNA, or DP receptor protein, or modulators of DP receptor activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose disorders in which modulation of DP receptor-related activity is indicated. The effective amount may vary according to a variety of factors such as the individual's condition, weight, sex and age. Other factors include the mode of administration. The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the DP receptor or its activity while minimizing any potential toxicity. In addition, co-administration or sequential administration of other agents may be desirable.

The present invention also has the objective of providing suitable topical, oral, systemic and parenteral pharmaceutical formulations for use in the methods of treatment of the present invention. The compositions containing compounds identified according to this invention as the active ingredient for use in the modulation of DP receptors can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a DP receptor modulating agent.

The daily dosage of the products may be varied over a wide range from 0.01 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages of the DP receptor modulators are adjusted when combined to achieve desired effects. On the other hand, dosages of these various agents may be independently optimized and combined to achieve a synergistic result wherein the pathology is reduced more than it would be if either agent were used alone.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For use in animals the compounds may be administered internally either orally or by injection, or topically as a liquid drench or as a shampoo.

For oral administration, the compounds may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds is possible through the use of a liquid drench or a shampoo containing the instant compounds as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds.

The compounds are primarily useful as agents for the treatment and/or prevention of DP receptor-mediated diseases in domestic animals such as cattle, sheep, horses, dogs, cats, goats, swine, and poultry. In treating such DP receptor-mediated diseases the compounds may be used individually or in combination with each other or with other unrelated agents. The dosage of the compounds required for best results depends on several factors such as the species and size of the animal, the type and severity of the infection, the method of administration and the compound used. Oral administration of the compounds at a dose level of from 0.0005 to 10 mg per kg of animal body weight, either in a single dose or in several doses spaced a few days apart, generally gives good results. The techniques for administering these compounds to animals are known to those skilled in the veterinary field.

The following examples are provided for the purpose of illustrating the present invention without, however, limiting the same thereto.

EXAMPLE 1

Cloning of the DP cDNA

In order to clone the human DP prostanoid receptor a mouse DP receptor DNA probe was first generated using the poymerase chain reaction (PCR) as described below. Two degenerate oligonucleotides were synthesized (Research Genetics, Cambridge, Mass.) based on the mouse DP receptor amino acid sequence which was presented by Dr. Shuh Narumiya from Kyoto University, Japan, at the 9th International Conference on Prostaglandins and Related Compounds, Florence, Italy, Jun. 6–10, 1994 and subsequently published (Hirata M., et al. PNAS 91:11192–11196, 1994). The 5' sense oligonucleotide [5'-ATG AA(T,C) GA(G,A) (T,A)(G,C)I TA(T,C) (A,C)GI TG(T,C) CA-3'] (SEQ ID NO:1) was based on the first eight amino acids and the 3' antisense oligonuclootide [5'-AA (G,A)CA CCA IGT ICC IGG (G,A)CA (G,A)TA (T,C)TG-3'] (SEQ ID NO:2) was based on the nine amino acids which occur just after the putative transmembrane domain IV of the mouse DP receptor. The oligonucleotides were used to amplify a 549 base pair fragment using mouse genomic DNA as the template. The fragment was isolated from an agarose gel, labeled with $^{32}$P and used to screen a human genomic library (Clontech, Palo Alto, Calif.) using standard techniques (Sambrook et al.,1989. Molecular Cloning: A Laboratory Manual, 2nd Ed., Cold Spring Harbor Laboratory, Cold Spring Harbor, N.Y.). Positive phage clones were plaque purified and DNA was prepared by the plate lysate method (Sambrook et al., 1989. Molecular Cloning: A Laboratory Manual, 2nd Ed., Cold Spring Harbor Laboratory, Cold Spring Harbor, N.Y.). Phage DNA was digested with EcoRI and the resulting 3 kb fragment, coding for the 5'-end of the gene, was subcloned into the Bluescript vector pKS (Stratagene, La Jolla, Calif.). The first 1.5 kb of DNA was sequenced using an ABI automated sequencer, with KS and SK primers or primers generated from the determined sequences on both strands. This sequence was found to contain the 5' end of the coding region up to the intron in the end of the 6th transmembrane domain. The 3'-end of the genomic clone, subcloned into the Bluescript vector pKS as a 4.5 kb EcoRI/XhoI fragment, was sequenced and found to contain the coding region from the end of the 6th transmembrane domain until the end of the 7th transmembrane domain. Therefore, in order to obtain the missing 3' coding region 3' RACE-PCR was performed on a human small intestine cDNA library (Clontech). The full length coding cDNA was constructed as follows; the 5' end from the genomic clone and the 3' end from the RACE-PCR were ligated together at the common PstI site and subcloned into the Bluescript vector pKS. The nucleotide sequence of the hDP receptor is shown in FIG. 1. The amino acid sequence for the encoded protein is shown in FIG. 2. The 1.2 kb fragment (DP; FIG. 1) was found to contain some sequence identity with all other prostanoid receptors and the putative heptahelical arrangement characteristic of G protein-coupled receptors, was evident. A long open reading frame (approximately 1080 bp) was identified which encodes an approximately 359 amino acid polypeptide with a predicted relative molecular mass of about 40,276.

EXAMPLE 2
Construction of pcDNA3-hDP and pCEP4-hDP Mammalian Expression Vectors

Digestion of pKS-hDP with NotI and XhoI released a 1.2 kb cDNA which was subcloned into the same sites of either pcDNA3 or pCEP4, mammalian expression vectors (Invitrogen, San Diego, Calif.). The correct orientation was verified by BglII digestion.

EXAMPLE 3
Cloning of the DP cDNA into E. coli Expression Vectors

Recombinant DP is produced in E. coli following the transfer of the DP expression cassette into E. coli expression vectors, including but not limited to, the pET series (Novagen). The pET vectors place DP expression under control of the tightly regulated bacteriophage T7 promoter. Following transfer of this construct into an E. coli host which contains a chromosomal copy of T7 RNA polymerase gene driven by the inducible lac promoter, expression of DP is induced when an appropriate lac substrate (IPTG) is added to the culture. The levels of expressed DP are determined by the assays described above.

The cDNA encoding the entire open reading frame for DP is inserted into the NdeI site of pET 11a. Constructs in the positive orientation are identified by sequence analysis and used to transform the expression host strain BL21. Transformants are then used to inoculate cultures for the production of DP protein. Cultures may be grown in M9 or ZB media, whose formulation is known to those skilled in the art. After growth to an approximate $OD_{600}$=1.5, expression of DP is induced with 1 mM IPTG for 3 hours at 37° C. DP receptor binding activity will be found in membrane fractions from these cells.

EXAMPLE 4
In Vivo Translation of Synthetic DP mRNA by Xenopus Oocyte Microinjection and Expression in Mammalian Cells DP cDNA constructs are ligated into in vitro transcription vectors (the pGEM series, Promega) for the production of synthetic mRNAs.

Synthetic mRNA is produced in sufficient quantity in vitro by cloning double stranded DNA encoding DP MRNA into a plasmid vector containing a bacteriophage promoter, linearizing the plasmid vector containing the cloned DP-encoding DNA, and transcribing the cloned DNA in vitro using a DNA-dependent RNA polymerase from a bacteriophage that specifically recognizes the bacteriophage promoter on the plasmid vector.

Various plasmid vectors are available containing a bacteriophage promoter recognized by a bacteriophage DNA-dependent RNA polymerase, including but not limited to plasmids pSP64, pSP65, pSP70, pSP71, pSP72, pSP73, pGEM-3Z, pGEM-4Z, pGEM-3Zf, pGEM-5Zf, pGEM-7Zf, pGEM-9Zf, and pGEM-11Zf, the entire series of plasmids is commercially available from Promega.

The double stranded DP-encoding DNA is cloned into the bacteriophage promoter containing vector in the proper orientation using one or more of the available restriction endonuclease cloning sites on the vector which are convenient and appropriate for cloning DP DNA. The vector with the ligated DP DNA is used to transform bacteria, and clonal isolates are analyzed for the presence of the vector with the DP DNA in the proper orientation.

Once a vector containing the DP-encoding DNA in the proper orientation is identified and isolated, it is linearized by cleavage with a restriction endonuclease at a site downstream from, and without disrupting, the DP transcription unit. The linearized plasmid is isolated and purified, and used as a template for in vitro transcription of DP mRNA.

The template DNA is then mixed with bacteriophage-specific DNA-dependent RNA polymerase in a reaction mixture which allows transcription of the DNA template forming DP MRNA. Several bacteriophage-specific DNA-dependent RNA polymerases are available, including but not limited to T3, T7, and SP6 RNA polymerase. The synthetic DP MRNA is then isolated and purified.

It may be advantageous to synthesize mRNA containing a 5' terminal cap structure and a 3' poly A tail to improve mRNA stability. A cap structure, or 7-methylguanosine, may be incorporated at the 5' terminus of the MRNA by simply adding 7-methylguanosine to the reaction mixture with the DNA template. The DNA-dependent RNA polymerase incorporates the cap structure at the 5' terminus as it synthesizes the mRNA. The poly A tail is found naturally occurring in many cDNAs but can be added to the 3' terminus of the MRNA by simply inserting a poly A tail-encoding DNA sequence at the 3' end of the DNA template.

The isolated and purified DP mRNA is translated using either a cell-free system, including but not limited to rabbit reticulocyte lysate and wheat germ extracts (both commercially available from Promega and New England Nuclear) or in a cell based system, including but not limited to microinjection into Xenopus oocytes, with microinjection into Xenopus oocytes being preferred.

Xenopus oocytes are microinjected with a sufficient amount of synthetic DP MRNA to produce DP protein. The microinjected oocytes are incubated to allow translation of the DP mRNA, forming DP protein.

These synthetic mRNAs are injected into Xenopus oocytes (stage 5–6) by standard procedures [Gurdon, J. B. and Wickens, M. D. Methods in Enzymol. 101: 370–386, (1983)]. Oocytes are harvested and analyzed for DP expression as described below.

EXAMPLE 5
Cloning of DP cDNA into a Mammalian Expression Vector

DP cDNA expression cassettes are ligated at appropriate restriction endonuclease sites to the following vectors containing strong, universal mammalian promoters: pBC12BI [Cullen, B. R. Methods in Enzymol. 152: 684–704 1988], and pEE12 (CellTech EP O 338,841) and its derivatives pSZ9016-1 and p9019. p9019 represents the construction of a mammalian expression vector containing the hCMVIE promoter, polylinker and SV40 polyA element with a selectable marker/amplification system comprised of a mutant gene for dihydrofolate reductase (mDHFR) (Simonsen, C. C. and Levinson, A. D. Proc. Natl. Acad. Sci USA 80: 2495–2499 [1983]) driven by the SV40 early promoter. An SV40 polyadenylation sequence is generated by a PCR reaction defined by primers 13978-120 and 139778-121 using pD5 (Berker and Sharp, Nucl. Acid Res. 13: 841–857 [1985]) as template. The resulting 0.25 Kb PCR product is digested with ClaI and SpeI and ligated into the 6.7 Kb fragment of pEE12 which had been likewise digested. The resultant plasmid is digested with BglII and SfiI to liberate the 3' portion of the SV40 early promoter and the GScDNA from the vector. A 0.73 Kb Sfil-XhoII fragment isolated from plasmid pFR400 (Simonsen, C. C. and Levinson, A. D. Proc. Natl. Acad. Sci USA 80: 2495–2499 [1983]) is ligated to the 5.6 Kb vector described above, reconstituting the SV40 early promoter, and inserting the mdHFR gene. This plasmid is designated p9019. pSZ9016-1 is identical to p9019 except for the substitution of the HIV LTR for the huCMVIE promoter. This vector is constructed by digesting p9019 with XbaI and MluI to remove the huCMVIE promoter. The HIV LTR promoter, from residue −117 to +80 (as found in the vector pCD23 containing the portion of the HIV-1 LTR (Cullen, Cell 46:973[1986]) is PCR amplified from the plasmid pCD23 using oligonucleotide primers which appended to the ends of the product the MluI and SpeI restriction sites on the 5' side while Hind III and Xba I sites are appended on the 3' side. Following the digestion of the resulting 0.2 kb PCR product with the enzymes MluI and Xba I the fragment is agarose gel-purified and ligated into the 4.3 Kb promoterless DNA fragment to generate the vector pSZ9016-1.

Cassettes containing the DP cDNA in the positive orientation with respect to the promoter are ligated into appropriate restriction sites 3' of the promoter and identified by restriction site mapping and/or sequencing. These cDNA expression vectors are introduced into various host cells including, but not limited to: COS-7 (ATCC# CRL1651), CV-1 [Sackevitz et al., Science 238: 1575 (1987)], 293, L cells (ATCC# CRL6362)] by standard methods including but not limited to electroporation,or chemical procedures (cationic liposomes, DEAE dextran, calcium phosphate). Transfected cells and cell culture extracts can be harvested and analyzed for DP expression as described below.

All of the vectors used for mammalian transient expression can be used to establish stable cell lines expressing DP. Unaltered DP cDNA constructs cloned into expression vectors are expected to program host cells to make DP protein. The transfection host cells include, but are not limited to, CV-1 [Sackevitz et al., Science 238: 1575 (1987)], tk-L [Wigler, et al. Cell 11: 223 (1977)], NS/0, and dHFr-CHO [Kaufman and Sharp, J. Mol. Biol. 159: 601, (1982)].

Co-transfection of any vector containing DP cDNA with a drug selection plasmid including, but not limited to G418, aminoglycoside phosphotransferase, pLNCX [Miller, A. D. and Rosman G. J. Biotech News 7: 980–990 (1989)]; hygromycin, hygromycin-B phosphotransferase, pLG90 [Gritz. L. and Davies, J., GENE 25: 179 (1 983)]; APRT, xanthine-guanine phosphoribosyl-transferase, pMAM (Clontech) [Murray, et al., Gene 31: 233 (1984)] allows for the selection of stably transfected clones. Levels of DP are quantitated by the assays described herein.

DP cDNA constructs are ligated into vectors containing amplifiable drug-resistance markers for the production of mammalian cell clones synthesizing the highest possible levels of DP. Following introduction of these constructs into cells, clones containing the plasmid are selected with the appropriate agent, and isolation of an over-expressing clone with a high copy number of the plasmid is accomplished by selection in increasing doses of the agent. The following systems are utilized: the 9016 or the 9019 plasmid containing the mutant DHFR gene [Simonson, C. and Levinson, A., Proc. Natl. Acad. Sci. USA 80: 2495 (1983)], transfected into DHFR- CHO cells and selected in methotrexate; the pEE12 plasmid containing the glutamine synthetase gene, transfected into NS/O cells and selected in methionine sulfoximine (CellTech International Patent Application 2089/10404); and 9016 or other CMV promoter vectors, co-transfected with pDLAT-3 containing the thymidine kinase gene [Colbere and Garopin, F., Proc. Natl. Acad. Sci. 76: 3755 (1979)] in APRT and TK deficient L cells, selected in APRT (0.05 mM azaserine, 0.1 mM adenine, 4 ug/ml adenosine) and amplified with HAT (100 uM hypoxanthine, 0.4 uM aminopterin, 16 uM thymidine).

EXAMPLE 6

Expression of the DP Receptor in COS-M6 cells and [$^3$H] $PGD_2$ binding assays The recently cloned human prostaglandin $D_2$ (DP) receptor was subcloned into the pcDNA3 plasmid (Invitrogen) and transfected into COS-M6 cells by the cationic liposome-mediated transfer of DNA using LiofectAMINE reagent (GIBCO/BRL). The cells were maintained in culture for 72 h, then harvested and membranes prepared by differential centrifugation (1000×g for 10 min, then 100,000×g for 30 min) following lysis of the cells by nitrogen cavitation. [$^3$H]$PGD_2$ specific binding assays were performed in 10 mM BES adjusted to pH 7.0 with KOH and containing 1.0 mM EDTA, 10 mM $MnCl_2$, 0.87 nM [$^3$H]$PGD_2$ and 38 mg of protein from the 100,000×g membrane fraction. Incubations were conducted for 60 min at 30° C. prior to separation of the bound and free radioligand by rapid filtration through Whatman GF/B filters presoaked at 4° C. in washing buffer (10 mM BES/KOH (pH 7.0) containing 0.01% (w/v)bovine serum albumin). The filters were washed with approximately 16 ml of washing buffer and the residual [$^3$H]$PGD_2$ bound to the filter was quantified by liquid scintillation counting. Specific binding was defined as the difference between total binding and non-specific binding, determined in the presence of 1 mM $PGD_2$.

The cloned human DP receptor was transfected into COS-M6 cells and [$^3$H]$PGD_2$ binding assays were performed with membranes prepared from the transfected cells. The most effective competing ligand was the DP-agonist BW245C which displayed a Ki value of 0.9 nM. $PGD_2$ and the DP-antagonist BW868C were as potent with Ki values of 1.1 nM and 1.7 nM, respectively. Other prostaglandins and related analogues tested were at least 100-fold less active. $PGE_2$ displayed a Ki value of 101 nM, while $PGF_{2a}$ and iloprost had comparable activity with Ki values of 512 nM and 630 nM, respectively. The least active compound was the TP-selective agonist U46619 with a Ki value of approximately 1852 nM. The rank order of affinity for prostaglandins and related synthetic analogs at the human DP receptor was therefore: BW245C>$PGD_2$>BW868C>$PGE_2$>$PGF_{2a}$=iloprost>U46619. This rank order of potency has been predicted for the DP receptor from previous pharmacological studies.

EXAMPLE 7

Expression of the DP receptor in HEK293 (EBNA) cells and cAMP assays

The recently cloned human prostaglandin $D_2$ (DP) receptor was subcloned into the pCEP4 plasmid (Invitrogen) and transfected into HEK293 (EBNA) cells by the cationic liposome-mediated transfer of DNA using LipofectAMINE™ (Gibco/BRL) reagent. Cells were maintained in culture for 48 h post transfection and then trypsinized, diluted and replated in the presence 200 µg/ml hygromycin B (Calbiochem) to select for transfected cells. Cells were maintained under selection for 3 weeks to ensure a homogeneous population of cells expressing the DP receptor.

Increases in intracellular cAMP production following agonist challenge was performed in HEK293 (EBNA) cells expressing the DP receptor and control HEK293 (EBNA) cells. Cells were harvested at approximately 80% confluence by incubation in enzyme-free cell dissociation buffer (Gibco/BRL), washed once with HEPES-buffered Krebs-Ringer solution {1.25 mM $MgSO_4$, 1.5 mM $CaCl_2$, 5 mM KCl, 124 mM NaCl, 8 mM glucose, 1.25 mM $KH_2PO_4$, and 25 mM HEPES/KOH (pH 7.4)} and resuspended in the same buffer. The cAMP assay was performed in a final volume of 0.2 ml of HEPES-buffer Krebs-Ringer solution and 100 µM of the phosphodiesterase type IV inhibitor RO-20-1724 (Biomol), to prevent hydrolysis of cAMP. RO-20-1724 and the compounds under evaluation were added to the incubation mixture in dimethyl sulfoxide or ethanol to a final vehicle concentration 0.35% (v/v) which was kept constant in all samples. The reaction was initiated by the addition of $1.5 \times 10^5$ cells per incubation. Samples were incubated at 37° C. for 15 min and the reaction was then terminated by immersing the samples in boiling water for 3 minutes. Cell viability was always ≧96% as determined by trypan blue exclusion. Measurement of cAMP was performed by radioimmunoassay using [$^{125}$I]cAMP (Amersham International).

cAMP production was measured after challenge with prostanoids and related synthetic analogs in HEK293 (EBNA) cells expressing the DP receptor. The DP-selective agonist BW245C was the most potent compound to increase intracellular cAMP production with an $EC_{50}$ of 0.6 nM. $PGD_2$ was 10-fold less potent with an $EC_{50}$ value of 6.4 nM. The putative DP-selective antagonist BWA868C marginally increased cAMP production (20 pmol cAMP/$1.5 \times 10^5$ cells verses >140 pmol cAMP/$1.5 \times 10^5$ cells for $PGD_2$) at concentrations up to 1 µM. $PGE_2$, $PGE_1$, the stable prostacyclin mimetic iloprost and the thromboxane analog U46619 all had $EC_{50}$ values of >500 nM. The rank order of potency of prostaglandins and related synthetic analogs was therefore: BW245C>$PGD_2$>>$PGE_2$>$PGE_1$>$PGF_{2\alpha}$>iloprost=U46619. This rank order of potency has been predicted for the DP receptor from previous phamacological studies (Coleman et al., 1994, supra). Of all the prostanoids and synthetic related analogues tested in control HEK293 (EBNA) cells only challenge with $PGE_2$ or $PGE_1$ (1 µM) resulted in an increase in cAMP production to 6 pmoles/$1.5 \times 10^5$ cells, 14-fold less than detected in similarily challenged DP-expressing HEK293 (EBNA) cells. This increase seen in control cells is most likely a result of activation of endogenous prostanoid receptors.

EXAMPLE 8

Intracellular calcium assays in HEK293 (EBNA) cells expressing the DP receptor

Intracellular calcium $[Ca^{2+}]_i$ measurements were performed with both the DP-HEK293 (EBNA) stable cell line and control HEK293 (EBNA) cells. The cells were harvested with enzyme-free cell dissociation buffer, recovered by centrifugation at 300×g for 5 min at 22° C. and resuspended at $2 \times 10^6$ cells/ml in DMEM growth medium without G418 or hygromycin B. The cells were incubated at 37° C., 6% $CO_2$ for 45 min with 2 µM fura-2 AM. Unincorporated fura-2 AM was removed by three washes in HBSS (1.3 mM $CaCl_2$, 5 mM KCl, 0.3 mM $KH_2PO_4$, 0.9 mM $MgCl_2$, 138 mM NaCl, 4 mM $NaHCO_3$, 0.3 mM $Na_2HPO_4$, 5.6 mM D-glucose) by centrifugation at 300×g, for 5 min at 22° C. The cells were then resuspended at a final concentration of $10^6$ cells/ml in HBSS. $[Ca^{2+}]_i$ was measured following agonist challenge of $2*10^6$ fura-2 AM loaded cells using a Perkin-Elmer LS-5 spectrophotometer essentially as described (Chan et al., 1994, Journal of Pharmacology and Experimental Therapeutics 269(3): 891–896).

The addition of 10 to 1000 nM $PGD_2$ increased calcium mobilization in HEK293 (EBNA) cells expressing the DP receptor in a concentration-dependent manner. Concentrations below 10 nM failed to induce a response which was significantly different from the vehicle. The addition of 1000 nM $PGD_2$ to control cells did not provoke any change in $[Ca^{2+}]_i$ which demonstrates that the increase in $[Ca^{2+}]_i$ is mediated through the DP receptor. Cells were viable at the end of each experiment, as monitored by the large increase in $[Ca^{2+}]_i$ observed upon challenge with 0.5 µM of the calcium ionophore ionomycin, followed by quenching of the $[Ca^{2+}]_i$ response upon addition of 1 mM EDTA.

EXAMPLE 9

Cloning of DP cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). Recombinant baculoviruses expressing DP cDNA are produced by the following standard methods (InVitrogen Maxbac Manual): the DP cDNA constructs are ligated downstream of the polyhedrin promoter in a variety of baculovirus transfer vectors, including the pAC360 and the pBlueBac vector (InVitrogen). Recombinant baculoviruses are generated by homologous recombination following co-transfection of the baculovirus transfer vector and linearized AcNPV genomic DNA [Kitts, P. A., Nuc. Acid. Res. 18: 5667 (1990)] into Sf9 cells. Recombinant pAC360 viruses are identified by the absence of inclusion bodies in infected cells (Summers, M. D. and Smith, G. E., Texas Agriculture Exp. Station Bulletin No. 1555) and recombinant pBlueBac viruses are identified on the basis of b-galactosidase expression (Vialard, et al. 1990, J. Virol., 64, pp 37–50). Following plaque purification and infection of sf9 cells with DP recombinant baculovirus, DP expression is measured by the assays described above.

The cDNA encoding the entire open reading frame for DP is inserted into the BamHI site of pBlueBacII. Constructs in the positive orientation with respect to the polyhedrin promoter are identified by sequence analysis and used to transfect Sf9 cells in the presence of linear AcNPV wild type DNA.

Authentic, active DP is found associated with the membranes of infected cells. Membrane preparations are prepared from infected cells by standard procedures.

EXAMPLE 10

Cloning of DP cDNA into a yeast expression vector

Recombinant DP is produced in the yeast S. cerevisiae following the insertion of the optimal DP cDNA construct into expression vectors designed to direct the intracellular expression of heterologous proteins. For intracellular expression, vectors such as EmBLyex4 or the like are ligated to the DP cistron [Rinas, U. et al., Biotechnology 8: 543–545 (1990); Horowitz B. et al., J. Biol. Chem. 265: 4189–4192 (1989)]. The levels of expressed DP are determined by the assays described above.

EXAMPLE 11

Purification of Recombinant DP

Recombinantly produced DP may be purified by antibody affinity chromatography.

DP antibody affinity columns are made by adding the anti-DP antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing solubilized DP is slowly passed through the column. The column is then washed with phosphate-buffered saline together with detergents until the optical density (A280) falls to background, then the protein is eluted with 0.23 M glycine-HCl (pH 2.6) together with detergents. The purified DP protein is then dialyzed against phosphate buffered saline together with detergents.

What is claimed is:

1. A method of determining whether a test compound modulates a signal transduction activity of a prostaglandin receptor DP, comprising:
   a) culturing DP-receptor-expressing host cells under conditions that would allow expression of a recombinant prostaglandin receptor, said host cells being transfected with a nucleic acid molecule encoding said recombinant prostaglandin DP-receptor comprising the amino acid sequence as set forth in SEQ ID NO:3;
   b) exposing the DP receptor-expressing host cells of step a) to the test compound;
   c) exposing control host cells to the test compound of step b), wherein said control host cells do not express recombinant prostaglandin DP receptor protein;
   d) measuring the modulating affect of the test compound which interacts with the recombinant DP receptor from the host cells of step a) and control host cells of step c); and,
   e) comparing the modulating affect of the test compound on the host cells and control host cells.

2. The method of claim 1 wherein the nucleic acid molecule is DNA, wherein said DP receptor-expressing host cells are transiently or stably transformed by said DNA molecule.

3. The method of claim 2 wherein said host cells are COS-M6 cells.

4. A method of determining whether a test compound modulates a signal tranduction activity of a prostaglandin receptor DP, comprising:
   a) culturing DP-receptor-expressing host cells under conditions that would allow expression of a recombinant prostaglandin receptor, said host cells being transfected with a nucleic acid molecule encoding said recombinant prostaglandin DP-receptor comprising the amino acid sequence as set forth in SEQ ID NO:3;
   b) exposing a first population of DP receptor-expressing cells of step a) to a known prostaglandin DP receptor ligand;
   c) exposing a second population of DP receptor-expressing cells of step a) to the test compound and the known prostaglandin DP-receptor ligand of step b);
   d) exposing control host cells to the test compound of step c), wherein said control host cells do not express recombinant prostaglandin DP receptor protein;
   e) measuring the modulating affect of the test compound, which interacts with recombinant DP protein, in the presence and absence of the known DP receptor ligand, from the cells of step b), step c) and step d); and,
   f) comparing the modulating affect of the test compound as determined from step b), step c) and step d.

5. The method of claim 4 wherein the nucleic acid molecule is DNA, wherein said DP receptor-expressing host cells are transiently or stably transformed by said DNA molecule.

6. The method of claim 5 wherein said host cells are COS-M6 cells.

7. The method of claim 4 wherein said known prostaglandin DP receptor ligand is a ligand which shows 50% maximum specific binding to the prostaglandin DP receptor protein at a ligand concentration of up to 0.01 $\mu$M when competing with labeled $PGD_2$ for binding to the prostaglandin DP receptor protein.

8. The method of claim 7 wherein said known, labeled prostaglandin DP receptor ligand is selected from the group consisting of BW245C, $PGD_2$ and BW868C.

9. A method of determining whether a test compound competes with a known prostaglandin DP receptor ligand for binding to a prostaglandin DP receptor protein, comprising:
   a) culturing DP-receptor-expressing host cells under conditions that would allow expression of a recombinant prostaglandin receptor, said host cells being transfected with a nucleic acid molecule encoding said recombinant prostaglandin DP-receptor comprising the amino acid sequence as set forth in SEQ ID NO:3;
   b) isolating a substantially purified cell membrane preparation from the DP receptor-expressing cells of step a);
   c) exposing a first population of the purified cell membrane preparation of step b) to a known, labeled prostaglandin DP receptor ligand;
   d) exposing a second population of the purified cell membrane preparation of step b) to the test compound and the known, labeled prostaglandin DP receptor ligand;
   e) determining the binding of the known, labeled prostaglandin DP receptor ligand to the membrane preparations of step c) and step d); and,
   f) comparing the binding of the known, labeled prostaglandin DP receptor ligand protein to the membrane preparations of step c) and step d).

10. The method of claim 9 wherein said known prostaglandin DP receptor ligand is a ligand which shows 50% maximum specific binding to the prostaglandin DP receptor protein at a ligand concentration of up to 0.01 $\mu$M when competing with labeled $PGD_2$ for binding to the prostaglandin DP receptor protein.

11. The method of claim 10 wherein said known, labeled prostaglandin DP receptor ligand is selected from the group consisting of BW245C, $PGD_2$ and BW868C.

12. A method of determining whether a test compound competes with a known prostaglandin DP receptor ligand for binding to a prostaglandin DP receptor protein, comprising:
   a) culturing DP-receptor-expressing host cells under conditions that would allow expression of a recombinant prostaglandin receptor, said host cells being transfected with a nucleic acid molecule encoding said recombinant prostaglandin DP-receptor comprising the amino acid sequence as set forth in SEQ ID NO:3;
   b) lysing the DP receptor expressing host cells of step a);
   c) exposing a first population of the lysed cells of step b) to a known, labeled prostaglandin DP receptor ligand;
   d) exposing a second population of the lysed cells of step b) to the test compound and the known, labeled prostaglandin DP receptor ligand;
   e) determining the binding of the known, labeled prostaglandin DP receptor ligand to the DP receptor from the lysed cells of step c) and step d); and,
   f) comparing the binding of the known, labeled prostaglandin DP receptor ligand protein to the DP receptor from the lysed cells of step c) and step d).

13. The method of claim 12 wherein said known prostaglandin DP receptor ligand is a ligand which shows 50% maximum specific binding to the prostaglandin DP receptor protein at a ligand concentration of up to 0.01 $\mu$M when competing with labeled $PGD_2$ for binding to the prostaglandin DP receptor protein.

14. The method of claim 13 wherein said known, labeled prostaglandin DP receptor ligand is selected from the group consisting of BW245C, $PGD_2$ and BW868C.

15. A method of determining whether a test compound competes with a known prostaglandin DP receptor ligand for binding to a prostaglandin DP receptor protein, comprising:
   a) culturing DP-receptor-expressing host cells under conditions that would allow expression of a recombinant prostaglandin receptor, said host cells being transfected with a nucleic acid molecule encoding said recombinant prostaglandin DP-receptor comprising the amino acid sequence as set forth in SEQ ID NO:3;
   b) exposing a first population of DP receptor-expressing cells of step a) to a known, labeled prostaglandin DP receptor ligand;
   c) exposing a second population of DP receptor-expressing cells of step a) to the compound and the known, labeled prostaglandin DP-receptor ligand of step b);
   d) determining the binding of the known, labeled prostaglandin DP receptor ligand to the membrane preparations of step b) and step c); and,
   e) comparing the binding of the known, labeled prostaglandin DP receptor ligand protein to the membrane preparations of step b) and step c).

16. The method of claim 15 wherein said known prostaglandin DP receptor ligand is a ligand which shows 50% maximum specific binding to the prostaglandin DP receptor protein at a ligand concentration of up to 0.01 $\mu$M when competing with labeled $PGD_2$ for binding to the prostaglandin DP receptor protein.

17. The method of claim 16 wherein said known, labeled prostaglandin DP receptor ligand is selected from the group consisting of BW245C, $PGD_2$ and BW868C.

* * * * *

```
                          SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 1:

ATGAAYGARW SNTAYMGNTG YCA                                          23

(2) INFORMATION FOR SEQ ID NO: 2:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 2:

AARCACCANG TNCCNGGRCA RTAYTG                                       26

(2) INFORMATION FOR SEQ ID NO: 3:

(i) SEQUENCE CHARACTERISTICS:
          (A) LENGTH: 359 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO: 3:

Met Lys Ser Pro Phe Tyr Arg Cys Gln Asn Thr Thr Ser Val Glu Lys
1               5                   10                  15

Gly Asn Ser Ala Val Met Gly Gly Val Leu Phe Ser Thr Gly Leu Leu
            20                  25                  30

Gly Asn Leu Leu Ala Leu Gly Leu Leu Ala Arg Ser Gly Leu Gly Trp
        35                  40                  45

Cys Ser Arg Arg Pro Leu Arg Pro Leu Pro Ser Val Phe Tyr Met Leu
    50                  55                  60

Val Cys Gly Leu Thr Val Thr Asp Leu Leu Gly Lys Cys Leu Leu Ser
65                  70                  75                  80
```

```
Pro Val Val Leu Ala Ala Tyr Ala Gln Asn Arg Ser Leu Arg Val Leu
                85                  90                  95

Ala Pro Ala Leu Asp Asn Ser Leu Cys Gln Ala Phe Ala Phe Phe Met
            100                 105                 110

Ser Phe Phe Gly Leu Ser Ser Thr Leu Gln Leu Leu Ala Met Ala Leu
        115                 120                 125

Glu Cys Trp Leu Ser Leu Gly His Pro Phe Phe Tyr Arg Arg His Ile
    130                 135                 140

Thr Leu Arg Leu Gly Ala Leu Val Ala Pro Val Val Ser Ala Phe Ser
145                 150                 155                 160

Leu Ala Phe Cys Ala Leu Pro Phe Met Gly Phe Gly Lys Phe Val Gln
                165                 170                 175

Tyr Cys Pro Gly Thr Trp Cys Phe Ile Gln Met Val His Glu Glu Gly
            180                 185                 190

Ser Leu Ser Val Leu Gly Tyr Ser Val Leu Tyr Ser Ser Leu Met Ala
        195                 200                 205

Leu Leu Val Leu Ala Thr Val Leu Cys Asn Leu Gly Ala Met Arg Asn
    210                 215                 220

Leu Tyr Ala Met His Arg Arg Leu Gln Arg His Pro Arg Ser Cys Thr
225                 230                 235                 240

Arg Asp Cys Ala Glu Pro Arg Ala Asp Gly Arg Glu Ala Ser Pro Gln
                245                 250                 255

Pro Leu Glu Glu Leu Asp His Leu Leu Leu Ala Leu Met Thr Val
            260                 265                 270

Leu Phe Thr Met Cys Ser Leu Pro Val Ile Tyr Arg Ala Tyr Tyr Gly
        275                 280                 285

Ala Phe Lys Asp Val Lys Glu Lys Asn Arg Thr Ser Glu Glu Ala Glu
    290                 295                 300

Asp Leu Arg Ala Leu Arg Phe Leu Ser Val Ile Ser Ile Val Asp Pro
305                 310                 315                 320

Trp Ile Phe Ile Ile Phe Arg Ser Pro Val Phe Arg Ile Phe Phe His
                325                 330                 335

Lys Ile Phe Ile Arg Pro Leu Arg Tyr Arg Ser Arg Cys Ser Asn Ser
            340                 345                 350

Thr Asn Met Glu Ser Ser Leu
            355

(2) INFORMATION FOR SEQ ID NO: 4:

(i) SEQUENCE CHARACTERISTICS:
        (A) LENGTH: 1488 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

GAATTCTGGC TATTTTCCTC CTGCCGTTCC GACTCGGCAC CAGAGTCTGT CTCTACTGAG      60

AACGCAGCGC GTCAGGGCCG AGCTCTTCAC TGGCCTGCTC CGCGCTCTTC AATGCCAGCG     120

CCAGGCGCTC ACCCTGCAGA GCGTCCCGCC TCTCAAAGAG GGGTGTGACC CGCGAGTTTA     180

GATAGGAGGT TCCTGCCGTG GGAACACCC CGCCGCCCTC GGAGCTTTTT CTGTGGCGCA      240

GCTTCTCCGC CCGAGCCGCG CGCGGAGCTG CCGGGGGCTC CTTAGCACCC GGGCGCCGGG     300

GCCCTCGCCC TTCCGCAGCC TTCACTCCAG CCCTCTGCTC CCGCACGCCA TGAAGTCGCC     360
```

-continued

| | | | | | |
|---|---|---|---|---|---|
| GTTCTACCGC | TGCCAGAACA | CCACCTCTGT | GGAAAAAGGC | AACTCGGCGG | TGATGGGCGG | 420 |
| GGTGCTCTTC | AGCACCGGCC | TCCTGGGCAA | CCTGCTGGCC | CTGGGCTGC | TGGCGCGCTC | 480 |
| GGGGCTGGGG | TGGTGCTCGC | GGCGTCCACT | GCGCCCGCTG | CCCTCGGTCT | TCTACATGCT | 540 |
| GGTGTGTGGC | CTGACGGTCA | CCGACTTGCT | GGGCAAGTGC | CTCCTAAGCC | CGGTGGTGCT | 600 |
| GGCTGCCTAC | GCTCAGAACC | GGAGTCTGCG | GGTGCTTGCG | CCCGCATTGG | ACAACTCGTT | 660 |
| GTGCCAAGCC | TTCGCCTTCT | TCATGTCCTT | CTTTGGGCTC | TCCTCGACAC | TGCAACTCCT | 720 |
| GGCCATGGCA | CTGGAGTGCT | GGCTCTCCCT | AGGGCACCCT | TTCTTCTACC | GACGGCACAT | 780 |
| CACCCTGCGC | CTGGGCGCAC | TGGTGGCCCC | GGTGGTGAGC | GCCTTCTCCC | TGGCTTTCTG | 840 |
| CGCGCTACCT | TTCATGGGCT | TCGGGAAGTT | CGTGCAGTAC | TGCCCCGGCA | CCTGGTGCTT | 900 |
| TATCCAGATG | GTCCACGAGG | AGGGCTCGCT | GTCGGTGCTG | GGGTACTCTG | TGCTCTACTC | 960 |
| CAGCCTCATG | GCGCTGCTGG | TCCTCGCCAC | CGTGCTGTGC | AACCTCGGCG | CCATGCGCAA | 1020 |
| CCTCTATGCG | ATGCACCGGC | GGCTGCAGCG | GCACCCGCGC | TCCTGCACCA | GGGACTGTGC | 1080 |
| CGAGCCGCGC | GCGGACGGGA | GGGAAGCGTC | CCCTCAGCCC | CTGGAGGAGC | TGGATCACCT | 1140 |
| CCTGCTGCTG | GCGCTGATGA | CCGTGCTCTT | CACTATGTGT | TCTCTGCCCG | TAATTTATCG | 1200 |
| CGCTTACTAT | GGAGCATTTA | AGGATGTCAA | GGAGAAAAAC | AGGACCCTG | AAGAAGCAGA | 1260 |
| AGACCTCCGA | GCCTTGCGAT | TTCTATCTGT | GATTTCAATT | GTGGACCCTT | GGATTTTTAT | 1320 |
| CATTTTCAGA | TCTCCAGTAT | TTCGGATATT | TTTTCACAAG | ATTTTCATTA | GACCTCTTAG | 1380 |
| GTACAGGAGC | CGGTGCAGCA | ATTCCACTAA | CATGGAATCC | AGTCTGTGAC | AGTGTTTTTC | 1440 |
| ACTCTGTGGT | AAGCTGAGGA | ATATGTCACA | TTTTCAGTCA | AAGAACCA | | 1488 |